United States Patent
Sun et al.

(10) Patent No.: US 8,987,536 B2
(45) Date of Patent: Mar. 24, 2015

(54) PROCESS FOR THE REDUCTION OF R$_f$CCX IMPURITIES IN FLUOROOLEFINS

(71) Applicant: E. I. du Pont de Nemours and Company, Wilmington, DE (US)

(72) Inventors: Xuehui Sun, Swedesboro, NJ (US); Mario Joseph Nappa, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 99 days.

(21) Appl. No.: 13/911,444

(22) Filed: Jun. 6, 2013

(65) Prior Publication Data

US 2014/0018582 A1 Jan. 16, 2014

Related U.S. Application Data

(60) Provisional application No. 61/656,125, filed on Jun. 6, 2012.

(51) Int. Cl.

| | |
|---|---|
| *C07C 17/38* | (2006.01) |
| *C07C 17/25* | (2006.01) |
| *C07C 21/18* | (2006.01) |
| *C07C 17/20* | (2006.01) |
| *C07B 63/00* | (2006.01) |

(52) U.S. Cl.
CPC .................. *C07C 17/25* (2013.01); *C07C 17/38* (2013.01); *C07C 17/206* (2013.01); *C07B 63/00* (2013.01)
USPC ............ 570/177; 570/155; 570/262; 570/238

(58) Field of Classification Search
CPC ...... C07C 17/38; C07C 21/18; C07C 17/383; C07C 17/25; C07C 17/206
USPC ......... 570/177, 178, 155, 262, 164, 238, 153, 570/226
See application file for complete search history.

(56) References Cited

U.S. PATENT DOCUMENTS

| | | |
|---|---|---|
| 5,563,306 A | 10/1996 | Meinert |
| 2009/0240090 A1 | 9/2009 | Merkel et al. |
| 2010/0029997 A1* | 2/2010 | Wang et al. ................... 570/134 |
| 2010/0185029 A1* | 7/2010 | Elsheikh et al. .............. 570/157 |
| 2010/0193347 A1 | 8/2010 | Hulse et al. |
| 2011/0105809 A1 | 5/2011 | Devic et al. |
| 2011/0155942 A1 | 6/2011 | Pigamo et al. |

OTHER PUBLICATIONS

Stepanova, N. P. et al. Zhurnal Organicheskoi Khimii, 1988, pp. 692-699.*
Stepanova, N. P. et al. Zhurnal Organicheskoi Khimii, 1988, p. 1; English Abstract.*
International Search Report issued in International Application No. PCT/US2013/044418 mailed Sep. 16, 2013.

* cited by examiner

*Primary Examiner* — Fereydoun G Sajjadi
*Assistant Examiner* — Medhanit Bahta
(74) *Attorney, Agent, or Firm* — Scully, Scott, Murphy & Presser, P.C.

(57) ABSTRACT

The present disclosure relates to processes for reducing the concentration of R$_f$C≡CX impurities in fluoroolefins. The process involves: contacting a mixture comprising at least one fluoroolefin and at least one R$_f$C≡CX impurity with at least one amine to reduce the concentration of the at least one R$_f$C≡CX impurity in the mixture; wherein R$_f$ is a perfluorinated alkyl group, and X is H, F, Cl, Br or I. The present disclosure also relates to processes for making at least one hydrotetrafluoropropene product selected from the group consisting of CF$_3$CF═CH$_2$, CF$_3$CH═CHF, and mixtures thereof and reducing the concentration of CF$_3$C≡CH impurity generated during the process. The present disclosure also relates to processes for making at least one hydrochlorotrifluoropropene product selected from the group consisting of CF$_3$CCl═CH$_2$, CF$_3$CH═CHCl, and mixtures thereof and reducing the concentration of CF$_3$C≡CH impurity generated during the process.

31 Claims, No Drawings

US 8,987,536 B2

PROCESS FOR THE REDUCTION OF R$_f$CCX IMPURITIES IN FLUOROOLEFINS

CROSS REFERENCE TO RELATED APPLICATION

The present application is claiming benefit of provisional application having Ser. No. U.S. Ser. No. 61/656,125 filed on Jun. 6, 2012, the contents of which are incorporated by reference.

BACKGROUND

1. Field of the Disclosure

The present disclosure relates to a process for reducing the concentration of R$_f$C≡CX impurities in fluoroolefins by contact with an amine.

2. Description of Related Art

Many industries have been working for the past few decades to find replacements for the ozone depleting chlorofluorocarbons (CFCs) and hydrochlorofluorocarbons (HCFCs). The CFCs and HCFCs have been employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. In the search for replacements for these versatile compounds, many industries have turned to the use of hydrofluorocarbons (HFCs).

The HFCs do not contribute to the destruction of stratospheric ozone, but are of concern due to their contribution to the "greenhouse effect", i.e., they contribute to global warming. As a result of their contribution to global warming, the HFCs have come under scrutiny, and their widespread use may also be limited in the future. Thus, there is a need for chemical compounds that have both low ozone depleting potentials (ODPs) and low global warming potentials (GWPs).

BRIEF SUMMARY OF THE DISCLOSURE

The present disclosure provides a process comprising: contacting a mixture comprising at least one fluoroolefin and at least one R$_f$C≡CX impurity with at least one amine to reduce the concentration of said at least one R$_f$C≡CX impurity in said mixture; wherein R$_f$ is a perfluorinated alkyl group, and X is H, F, Cl, Br or I.

The present disclosure also provides a process for making at least one hydrotetrafluoropropene product selected from the group consisting of CF$_3$CF═CH$_2$, CF$_3$CH═CHF, and mixtures thereof. The process comprises: (a) dehydrohalogenating at least one starting material selected from the group consisting of CF$_3$CFClCH$_3$, CF$_3$CHFCH$_2$Cl, CF$_3$CHClCH$_2$F, CF$_3$CH$_2$CHFCl, CF$_3$CHFCH$_2$F, CF$_3$CH$_2$CF$_2$H, CF$_3$CF$_2$CH$_3$, and mixtures thereof to produce a product mixture comprising CF$_3$C≡CH impurity and said at least one hydrotetrafluoropropene product; (b) contacting said product mixture with at least one amine to reduce the concentration of said CF$_3$C≡CH impurity in said product mixture; and (c) recovering said at least one hydrotetrafluoropropene product having reduced concentration of said CF$_3$C≡CH impurity.

The present disclosure also provides a process for making at least one hydrochlorotrifluoropropene product selected from the group consisting of CF$_3$CCl═CH$_2$, CF$_3$CH═CHCl, and mixtures thereof. The process comprises: (a) dehydrohalogenating at least one starting material selected from the group consisting of CF$_3$CCl$_2$CH$_3$, CF$_3$CHClCH$_2$Cl, CF$_3$CHClCH$_2$F, CF$_3$CH$_2$CHCl$_2$, CF$_3$CHFCH$_2$Cl, CF$_3$CFClCH$_3$, CF$_3$CH$_2$CHFCl, and mixtures thereof to produce a product mixture comprising CF$_3$C≡CH impurity and said at least one hydrochlorotrifluoropropene product; (b) contacting said product mixture with at least one amine to reduce the concentration of said CF$_3$C≡CH impurity in said product mixture; and (c) recovering said at least one hydrochlorotrifluoropropene product having reduced concentration of said CF$_3$C≡CH impurity.

DETAILED DESCRIPTION

Fluoroolefins have been found to have low ODPs and low GWPs and have been regarded as potential replacements for HFCs in many applications. For example, CF$_3$CF═CH$_2$ (HFO-1234yf) and CF$_3$CH═CHF (HFO-1234ze), having zero ODPs and low GWPs, have been identified as potential refrigerants. For another example, CF$_3$CH═CHCl (HCFO-1233zd) and CF$_3$CCl═CH$_2$ (HCFO-1233xf), having low ODPs and low GWPs, may be used as foam expansion agents. HCFO-1233zd is also an intermediate in the production of HFO-1234ze, and HCFO-1233xf is an intermediate in the production of HFO-1234yf.

It has been found that R$_f$C≡CX impurities, such as CF$_3$C≡CH, are often present in the fluoroolefin products. Since R$_f$C≡CX impurities might be highly toxic, they need to be removed from the fluoroolefin products.

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

Before addressing details of embodiments described below, some terms are defined or clarified.

HFO-1234ze may exist as one of two configurational isomers, E or Z. HFO-1234ze as used herein refers to the isomers, E-HFO-1234ze or Z—HFO-1234ze, as well as any combinations or mixtures of such isomers.

HCFO-1233zd also may exist as one of two configurational isomers, E or Z. HCFO-1233zd as used herein refers to the isomers, E-HCFO-1233zd or Z—HCFO-1233zd, as well as any combinations or mixtures of such isomers.

$CF_3CF=CHCl$ (HCFO-1224yd) also may exist as one of two configurational isomers, E or Z. HCFO-1224yd as used herein refers to the isomers, E-HCFO-1224yd or Z—HCFO-1224yd, as well as any combinations or mixtures of such isomers.

$CF_3CCl=CHCl$ (HCFO-1223xd) also may exist as one of two configurational isomers, E or Z. HCFO-1223xd as used herein refers to the isomers, E-HCFO-1223xd or Z—HCFO-1223xd, as well as any combinations or mixtures of such isomers.

The term "$R_fC=CX$ impurity", as used herein, means the impurity of the formula $R_fC=CX$ present in a fluoroolefin product.

The term "fluoroolefin", as used herein, means a molecule containing hydrogen, carbon, optionally chlorine, fluorine, and a carbon-carbon double bond.

The term "hydrofluoroolefin", as used herein, means a molecule containing hydrogen, carbon, fluorine, and a carbon-carbon double bond.

The term "hydrochlorofluoroolefin", as used herein, means a molecule containing hydrogen, carbon, chlorine, fluorine, and a carbon-carbon double bond.

The term "alkyl", as used herein, either alone or in compound words such as "perfluorinated alkyl group", includes cyclic or acyclic and straight-chain or branched alkyl groups, such as, methyl, ethyl, n-propyl, i-propyl, or the different isomers thereof.

The term "perfluorinated alkyl group", as used herein, means an alkyl group wherein all hydrogens on carbon atoms have been substituted by fluorines. Examples of a perfluorinated alkyl group include —$CF_3$ and —$CF_2CF_3$.

The term "amine", as used herein, means a chemical compound or a functional group that contains a basic nitrogen atom with a lone pair of electrons.

The term "aralkyl", as used herein, means an alkyl group wherein one or more hydrogens on carbon atoms have been substituted by an aryl group. Examples of an aralkyl group include $C_6H_5CH_2$—.

The term "heteroalkyl", as used herein, means an alkyl group wherein one or more carbon atoms of the alkyl backbone have been substituted by a heteroatom, such as, O, S or N. Examples of heteroalkyl groups include $CH_3CH_2CH_2NHCH_2CH_2$—, $CH_3CH_2CH_2OCH_2CH_2$—, The term "polyamine", as used herein, means an organic compound having two or more primary amino groups (—$NH_2$).

The term "heterocyclic compound", as used herein, means a cyclic organic compound that has atoms of at least two different elements as members of its ring(s).

The term "heterocyclic amine", as used herein, means a heterocyclic compound wherein at least one member of its ring(s) is amine nitrogen and at least two members of its ring(s) are carbon.

The term "aliphatic amine", as used herein, means an amine wherein the groups attached to nitrogen are aliphatic.

The term "ppm", as used herein, means parts per million by weight.

The term "ppm-molar", as used herein, means parts per million by mole.

The term "substantially free", as used herein, means that the fluoroolefin contains 2 ppm-molar or less of the $R_fC=CX$ impurity.

The term "dehydrohalogenation", as used herein, means dehydrofluorination or dehydrochlorination. The term "dehydrohalogenating", as used herein, means dehydrofluorinating or dehydrochlorinating. The term "dehydrohalogenated", as used herein, means dehydrofluorinated or dehydrochlorinated.

The term "dehydrofluorination", "dehydrofluorinating" or "dehydrofluorinated", as used herein, means a process during which hydrogen and fluorine on adjacent carbons in a molecule are removed.

The term "dehydrochlorination", "dehydrochlorinating", or "dehydrochlorinated", as used herein, means a process during which hydrogen and chlorine on adjacent carbons in a molecule are removed.

The term "phase transfer catalyst", as used herein, means a substance that facilitates the migration of a chemical compound from one phase into another phase. In some embodiments of this invention, the phase transfer catalyst is selected from the group consisting of crown ethers, onium salts, cryptands, polyalkylene glycols, and mixtures and derivatives thereof. The phase transfer catalyst can be ionic or neutral. In some embodiments of this invention, onium salts include quaternary phosphonium salts and quaternary ammonium salts. Examples of quaternary ammonium salts include tetra-n-butylammonium hydroxide, tetramethylammonium chloride, tetramethylammonium bromide, benzyltriethylammonium chloride, methyltri-n-octylammonium chloride (also known as Aliquat™ 336), dodecyltrimethylammonium bromide, tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide, triphenylmethylphosphonium chloride, and mixtures thereof. In this disclosure, a phase transfer catalyst might be used in the contacting step process to help removing the $R_fC=CX$ impurity from the fluoroolefin. A phase transfer catalyst might also be used in the dehydrohalogenation process with the basic aqueous solution.

The present disclosure provides a process for reducing the amount of $R_fC=CX$ impurity from fluoroolefin by contacting fluoroolefin containing $R_fC=CX$ impurity with amine. The process comprises: contacting a mixture comprising at least one fluoroolefin and at least one $R_fC=CX$ impurity with at least one amine to reduce the concentration of said at least one $R_fC=CX$ impurity in said mixture; wherein $R_f$ is a perfluorinated alkyl group, and X is H, F, Cl, Br or I. In some embodiments of this invention, the process further comprises recovering said at least one fluoroolefin having reduced concentration of said at least one $R_fC=CX$ impurity.

In some embodiments of this invention, the amount of the at least one fluoroolefin in the mixture is at least 50 wt % based on the total weight of the mixture. In some embodiments of this invention, the amount of the at least one fluoroolefin in the mixture is at least 70 wt % based on the total weight of the mixture. In some embodiments of this invention, the amount of the at least one fluoroolefin in the mixture is at least 90 wt % based on the total weight of the mixture. In some embodiments of this invention, the mixture consists essentially of the at least one fluoroolefin and the at least one $R_fC{\equiv}CX$ impurity.

A fluoroolefin in this disclosure can be a hydrofluoroolefin or a hydrochlorofluoroolefin. In some embodiments of this invention, the at least one fluoroolefin is hydrofluoroolefin. In some embodiments of this invention, the at least one fluoroolefin is hydrochlorofluoroolefin. In some embodiments of this invention, the at least one hydrofluoroolefin is selected from the group consisting of $CF_3CF{=}CH_2$ (HFO-1234yf), $CF_3CH{=}CHF$ (HFO-1234ze), $CF_3CH{=}CH_2$ (HFO-1243zf), $CF_3CH{=}CF_2$ (HFO-1225zc), $CF_3CF{=}CHF$ (HFO-1225ye), and mixtures thereof. In some embodiments of this invention, the at least one hydrochlorofluoroolefin is selected from the group consisting of $CF_3CCl{=}CH_2$ (HCFO-1233xf), $CF_3CH{=}CHCl$ (HCFO-1233zd), $CF_3CF{=}CHCl$ (HCFO-1224yd), $CF_3CH{=}CCl_2$ (HCFO-1223za), $CF_3CCl{=}CHCl$ (HCFO-1223xd), $CF_3CH{=}CFCl$, $CF_3CCl{=}CHF$, and mixtures thereof. In some embodiments of this invention, the at least one fluoroolefin is selected from the group consisting of $CF_3CF{=}CH_2$, $CF_3CH{=}CHF$, $CF_3CH{=}CH_2$, $CF_3CCl{=}CH_2$, $CF_3CH{=}CHCl$, $CF_3CH{=}CFCl$, $CF_3CH{=}CF_2$, $CF_3CCl{=}CHF$, $CF_3CF{=}CHF$, $CF_3CF{=}CHCl$, $CF_3CH{=}CCl_2$, $CF_3CCl{=}CHCl$, and mixtures thereof. In some embodiments of this invention, the hydrofluoroolefin is at least one hydrotetrafluoropropene product selected from the group consisting of $CF_3CF{=}CH_2$, $CF_3CH{=}CHF$, and mixtures thereof. In some embodiments of this invention, the hydrochlorofluoroolefin is at least one hydrochlorotrifluoropropene product selected from the group consisting of $CF_3CCl{=}CH_2$, $CF_3CH{=}CHCl$, and mixtures thereof.

During the processes of making fluoroolefin and its precursors, $R_fC{\equiv}CX$ impurities may be generated as byproducts. For example, during the dehydrochlorination process of $CF_3CFClCH_3$ (HCFC-244bb) to make HFO-1234yf, $CF_3C{\equiv}CH$ impurity has been found present in the product mixture with HFO-1234yf. $CF_3C{\equiv}CH$ impurity and/or $CF_3C{\equiv}CCl$ impurity may also be present in the HCFC-244bb starting material.

The $R_fC{\equiv}CX$ impurity that is removed from fluoroolefin by processes of this disclosure is a fluorinated terminal alkyne. In some embodiments of this invention, $R_f$ is $-CF_3$. In some embodiments of this invention, $R_f$ is $-CF_2CF_3$. In some embodiments of this invention, the at least one $R_fC{\equiv}CX$ impurity is selected from the group consisting of $CF_3C{\equiv}CH$, $CF_3C{\equiv}CCl$, $CF_3C{\equiv}CF$, and mixtures thereof. In some embodiments of this invention, the at least one $R_fC{\equiv}CX$ impurity is selected from the group consisting of $CF_3C{\equiv}CH$, $CF_3C{\equiv}CCl$, and mixtures thereof. In some embodiments of this invention, the at least one $R_fC{\equiv}CX$ impurity is $CF_3C{\equiv}CH$. In some embodiments of this invention, the at least one $R_fC{\equiv}CX$ impurity is $CF_3C{\equiv}CCl$.

In some embodiments of this invention, the at least one fluoroolefin is selected from the group consisting of $CF_3CF{=}CH_2$, $CF_3CH{=}CHF$, $CF_3CH{=}CH_2$, $CF_3CCl{=}CH_2$, $CF_3CH{=}CHCl$, $CF_3CH{=}CFCl$, $CF_3CH{=}CF_2$, $CF_3CCl{=}CHF$, $CF_3CF{=}CHF$, $CF_3CF{=}CHCl$, $CF_3CH{=}CCl_2$, $CF_3CCl{=}CHCl$, and mixtures thereof, and the at least one $R_fC{\equiv}CX$ impurity is selected from the group consisting of $CF_3C{\equiv}CH$, $CF_3C{\equiv}CCl$, $CF_3C{\equiv}CF$, and mixtures thereof.

In some embodiments of this invention, the at least one fluoroolefin is selected from the group consisting of $CF_3CF{=}CH_2$, $CF_3CH{=}CHF$, $CF_3CH{=}CH_2$, $CF_3CCl{=}CH_2$, $CF_3CH{=}CHCl$, $CF_3CF{=}CHCl$, and mixtures thereof, and the at least one $R_fC{\equiv}CX$ impurity is selected from the group consisting of $CF_3C{\equiv}CH$, $CF_3C{\equiv}CCl$, $CF_3C{\equiv}CF$, and mixtures thereof.

In some embodiments of this invention, the at least one fluoroolefin is $CF_3CH{=}CH_2$, and the at least one $R_fC{\equiv}CX$ impurity is selected from the group consisting of $CF_3C{\equiv}CH$, $CF_3C{\equiv}CCl$, $CF_3C{\equiv}CF$, and mixtures thereof.

In some embodiments of this invention, the at least one fluoroolefin is selected from the group consisting of $CF_3CF{=}CH_2$, $CF_3CH{=}CHF$, $CF_3CCl{=}CH_2$, $CF_3CH{=}CHCl$, and mixtures thereof, and the at least one $R_fC{\equiv}CX$ impurity is selected from the group consisting of $CF_3C{\equiv}CH$, $CF_3C{\equiv}CCl$, and mixtures thereof.

In some embodiments of this invention, the at least one fluoroolefin is selected from the group consisting of $CF_3CF{=}CH_2$, $CF_3CH{=}CHF$, $CF_3CCl{=}CH_2$, $CF_3CH{=}CHCl$, and mixtures thereof, and the at least one $R_fC{\equiv}CX$ impurity is $CF_3C{\equiv}CH$.

In some embodiments of this invention, the at least one fluoroolefin is $CF_3CF{=}CH_2$, and the at least one $R_fC{\equiv}CX$ impurity is selected from the group consisting of $CF_3C{\equiv}CH$, $CF_3C{\equiv}CCl$, and mixtures thereof.

In some embodiments of this invention, the at least one fluoroolefin is $CF_3CF{=}CH_2$, and the at least one $R_fC{\equiv}CX$ impurity is $CF_3C{\equiv}CH$.

In some embodiments of this invention, the at least one fluoroolefin is $CF_3CH{=}CHF$, and the at least one $R_fC{\equiv}CX$ impurity is selected from the group consisting of $CF_3C{\equiv}CH$, $CF_3C{\equiv}CCl$, and mixtures thereof.

In some embodiments of this invention, the at least one fluoroolefin is $CF_3CH{=}CHF$, and the at least one $R_fC{\equiv}CX$ impurity is $CF_3C{\equiv}CH$.

In some embodiments of this invention, the at least one fluoroolefin is a mixture of $CF_3CF{=}CH_2$ and $CF_3CH{=}CHF$, and the at least one $R_fC{\equiv}CX$ impurity is selected from the group consisting of $CF_3C{\equiv}CH$, $CF_3C{\equiv}CCl$, and mixtures thereof.

In some embodiments of this invention, the at least one fluoroolefin is a mixture of $CF_3CF{=}CH_2$ and $CF_3CH{=}CHF$, and the at least one $R_fC{\equiv}CX$ impurity is $CF_3C{\equiv}CH$.

In some embodiments of this invention, the at least one fluoroolefin is selected from the group consisting of $CF_3CCl{=}CH_2$, $CF_3CH{=}CHCl$, and mixtures thereof, and the at least one $R_fC{\equiv}CX$ impurity is selected from the group consisting of $CF_3C{\equiv}CH$, $CF_3C{\equiv}CCl$, and mixtures thereof.

In some embodiments of this invention, the at least one fluoroolefin is selected from the group consisting of $CF_3CCl{=}CH_2$, $CF_3CH{=}CHCl$, and mixtures thereof, and the at least one $R_fC{\equiv}CX$ impurity is $CF_3C{\equiv}CH$.

In some embodiments of this invention, the at least one fluoroolefin is $CF_3CH{=}CHCl$, and the at least one $R_fC{\equiv}CX$ impurity is selected from the group consisting of $CF_3C{\equiv}CH$, $CF_3C{\equiv}CCl$, and mixtures thereof.

In some embodiments of this invention, the at least one fluoroolefin is $CF_3CH{=}CHCl$, and the at least one $R_fC{\equiv}CX$ impurity is $CF_3C{\equiv}CH$.

In some embodiments of this invention, the at least one fluoroolefin is $CF_3CCl{=}CH_2$, and the at least one $R_fC{\equiv}CX$ impurity is selected from the group consisting of $CF_3C{\equiv}CH$, $CF_3C{\equiv}CCl$, and mixtures thereof.

In some embodiments of this invention, the at least one fluoroolefin is $CF_3CCl{=}CH_2$, and the at least one $R_fC{\equiv}CX$ impurity is $CF_3C{\equiv}CH$.

It has been found through experiments that $R_fC\equiv CX$ impurity can be removed from fluoroolefin by contacting with an amine.

In some embodiments of this invention, the at least one amine can be represented by the formula $R_3N$ wherein each R is independently a hydrogen, an alkyl group, a heteroalkyl group, an aryl group, or an aralkyl group. The alkyl group, heteroalkyl group, aryl group, and aralkyl group can be substituted or unsubstituted. Substituted alkyl group, substituted heteroalkyl group, substituted aryl group, or substituted aralkyl group herein means that one or more hydrogens on carbon atoms have been substituted by functional groups, such as hydroxyl groups, alkoxy groups, halogens, amino groups, etc. The at least one amine for this disclosure can be aliphatic amine, aromatic amine, or mixtures thereof. In some embodiments of this invention, the at least one amine is aliphatic amine.

In some embodiments of this invention, the at least one amine can be primary amine, secondary amine, tertiary amine, or mixtures thereof. In some embodiments of this invention, the at least one amine is primary unsubstituted alkyl amine of the formula $RNH_2$ wherein R is a $C_1$-$C_{16}$ unsubstituted alkyl group. In some embodiments of this invention, the at least one amine is primary unsubstituted alkyl amine of the formula $RNH_2$ wherein R is a $C_4$-$C_{12}$ unsubstituted alkyl group. Examples of primary unsubstituted alkyl amine include methylamine, ethylamine, propylamine, isopropylamine, butylamine, sec-butylamine, tert-butylamine, amylamine, isoamylamine, tert-amylamine, hexylamine, heptylamine, octylamine, tert-octylamine (1,1,3,3-tetramethylbutylamine), and mixtures thereof In some embodiments of this invention, the at least one amine is secondary unsubstituted alkyl amine of the formula $R_2NH$ wherein each R is independently a $C_1$-$C_{14}$ unsubstituted alkyl group. In some embodiments of this invention, the at least one amine is secondary unsubstituted alkyl amine of the formula $R_2NH$ wherein each R is independently a $C_3$-$C_{10}$ unsubstituted alkyl group. Examples of secondary unsubstituted alkyl amine include dimethylamine, diethylamine, dipropylamine, diisopropylamine, dibutylamine, di-sec-butylamine, diamylamine, dihexylamine, and mixtures thereof.

In some embodiments of this invention, the at least one amine is tertiary unsubstituted alkyl amine of the formula $R_3N$ wherein each R is independently a $C_1$-$C_{12}$ unsubstituted alkyl group. In some embodiments of this invention, the at least one amine is tertiary unsubstituted alkyl amine of the formula $R_3N$ wherein each R is independently a $C_2$-$C_8$ unsubstituted alkyl group. Examples of tertiary unsubstituted alkyl amine include trimethylamine, triethylamine, tripropylamine, tributylamine, triamylamine, trihexylamine, N,N-dimethylethylamine, N,N-dimethylpropylamine, N,N-dimethylbutylamine, and mixtures thereof.

In some embodiments of this invention, the at least one amine is selected from the group consisting of methylamine, dimethylamine, trimethylamine, ethylamine, diethylamine, triethylamine, propylamine, isopropylamine, dipropylamine, diisopropylamine, tripropylamine, butylamine, sec-butylamine, tert-butylamine, dibutylamine, tributylamine, di-sec-butylamine, amylamine, isoamylamine, tert-amylamine, diamylamine, triamylamine, hexylamine, dihexylamine, trihexylamine, heptylamine, octylamine, tert-octylamine (1,1,3,3-tetramethylbutylamine), N,N-dimethylethylamine, N,N-dimethylpropylamine, N,N-dimethylbutylamine, and mixtures thereof.

In some embodiments of this invention, at least one R group of the amine of the formula $R_3N$ is a $C_1$-$C_{16}$ substituted alkyl group wherein one or more hydrogens on carbon atoms have been substituted by hydroxyl groups, and the rest of the R groups, if any, are independently selected from the group consisting of hydrogen and $C_1$-$C_{16}$ unsubstituted alkyl groups. Examples of such amine include ethanolamine ($H_2NCH_2CH_2OH$), diethanolamine, triethanolamine, tris(hydroxymethyl)aminomethane (($HOCH_2)_3CNH_2$), 2-(methylamino)ethanol ($CH_3NHCH_2CH_2OH$), 2-(ethylamino)ethanol ($CH_3CH_2NHCH_2CH_2OH$), 2-(propylamino)ethanol ($CH_3CH_2CH_2NHCH_2CH_2OH$), 2-(isopropylamino)ethanol (($CH_3)_2CHNHCH_2CH_2OH$), 2-(butylamino)ethanol ($CH_3(CH_2)_3NHCH_2CH_2OH$), 2-(tert-butylamino)ethanol (($CH_3)_3CNHCH_2CH_2OH$), triisopropanolamine ($[CH_3CH(OH)CH_2]_3N$), N,N-dimethylethanolamine ($HOCH_2CH_2N(CH_3)_2$), 1-dimethylamino-2-propanol (($CH_3)_2NCH_2CH(OH)CH_3$), 3-dimethylamino-1-propanol (($CH_3)_2N(CH_2)_3OH$), 2-amino-2-methyl-1-propanol (($CH_3)_2C(NH_2)CH_2OH$), and mixtures thereof.

In some embodiments of this invention, one R group of the amine of the formula $R_3N$ is a $C_1$-$C_{16}$ substituted alkyl group wherein one or more hydrogens on carbon atoms have been substituted by hydroxyl groups, and the other two R groups are independently selected from the group consisting of hydrogen and $C_1$-$C_{16}$ unsubstituted alkyl groups. Examples of such amine include ethanolamine ($H_2NCH_2CH_2OH$), tris(hydroxymethyl)aminomethane (($HOCH_2)_3CNH_2$), 2-(methylamino)ethanol ($CH_3NHCH_2CH_2OH$), 2-(ethylamino)ethanol ($CH_3CH_2NHCH_2CH_2OH$), 2-(propylamino)ethanol ($CH_3CH_2CH_2NHCH_2CH_2OH$), 2-(isopropylamino)ethanol (($CH_3)_2CHNHCH_2CH_2OH$), 2-(butylamino)ethanol ($CH_3(CH_2)_3NHCH_2CH_2OH$), 2-(tert-butylamino)ethanol (($CH_3)_3CNHCH_2CH_2OH$), N,N-dimethylethanolamine ($HOCH_2CH_2N(CH_3)_2$), 1-dimethylamino-2-propanol (($CH_3)_2NCH_2CH(OH)CH_3$), 3-dimethylamino-1-propanol (($CH_3)_2N(CH_2)_3OH$), 2-amino-2-methyl-1-propanol (($CH_3)_2 C(NH_2)CH_2OH$), and mixtures thereof.

In some embodiments of this invention, at least one R group of the amine of the formula $R_3N$ is a $C_1$-$C_{16}$ substituted alkyl group wherein one or more hydrogens on carbon atoms have been substituted by amino groups, and the rest of the R groups, if any, are independently selected from the group consisting of hydrogen and $C_1$-$C_{16}$ unsubstituted alkyl groups. Examples of such amine include 3-(dimethylamino)propylamine (($CH_3)_2N(CH_2)_3NH_2$), 3-(diethylamino)propylamine (($C_2H_5)_2N(CH_2)_3NH_2$), and mixtures thereof.

In some embodiments of this invention, the at least one amine is polyamine. Examples of polyamine include ethylene diamine, 1,2-propylenediamine, 1,3-propylenediamine, 1,4-diaminobutane, 1,3-diaminopentane, 1,5-diaminopentane, 1,6-diaminohexane, 2-methyl-1,5-pentanediamine, spermidine (N-(3-aminopropyl)butane-1,4-diamine), spermine (N,N'-bis(3-aminopropyl)butane-1,4-diamine), diethylenetriamine, triethylenetetramine, and mixtures thereof.

In some embodiments of this invention, at least one R group of the amine of the formula $R_3N$ is a $C_2$-$C_{16}$ substituted heteroalkyl group wherein one or more hydrogens on carbon atoms have been substituted by hydroxyl groups, and the rest of the R groups, if any, are independently selected from the group consisting of hydrogen and $C_1$-$C_{16}$ unsubstituted alkyl groups. In some embodiments of this invention, at least one R group of the amine of the formula $R_3N$ is a $C_2$-$C_{16}$ substituted heteroalkyl group wherein the heteroatom of the heteroalkyl group is oxygen and wherein one or more hydrogens on carbon atoms have been substituted by hydroxyl groups, and the rest of the R groups, if any, are independently selected from the group consisting of hydrogen and $C_1$-$C_{16}$ unsubstituted alkyl groups. Examples of such amine include 2-[2-(dimethylamino)ethoxy]ethanol (($CH_3)_2$ NCH$_2$CH$_2$OCH$_2$CH$_2$OH), 2-(2-aminoethoxy)ethanol (H$_2$NCH$_2$CH$_2$OCH$_2$CH$_2$OH), and mixtures thereof.

In some embodiments of this invention, the at least one amine is heterocyclic amine Examples of heterocyclic amine include pyrrolidine and its derivatives, pyrroline (including 1-pyrroline, 2-pyrroline and 3-pyrroline) and its derivatives, piperidine and its derivatives, piperazine and its derivatives, morpholine and its derivatives, imidazole and its derivatives, pyrazole and its derivatives, pyridine and its derivatives, pyrimidine and its derivatives, pyridazine and its derivatives, pyrazine and its derivatives, bipyridine (including 2,2'-bipyridine, 4,4'-bipyridine, 2,3'-bipyridine, and 3,4'-bipyridine, etc.) and its derivatives, and mixtures thereof.

In some embodiments of this invention, the at least one amine is ammonia (NH$_3$). In some embodiments of this invention, the at least one amine is hydrazine (NH$_2$NH$_2$), hydrazine derivatives, or mixtures thereof. Examples of hydrazine derivatives include methylhydrazine (CH$_3$NHNH$_2$), 1,1-dimethylhydrazine ((CH$_3$)$_2$NNH$_2$), 1,2-dimethylhydrazine (CH$_3$NHNHCH$_3$), phenylhydrazine, 2,4-dinitrophenylhydrazine, and mixtures thereof.

In some embodiments of this invention, the at least one amine is aromatic amine. Examples of aromatic amine include aniline, o-toluidine, m-toluidine, p-toluidine, xylidine, 2,4,6-trimethylaniline, o-anisidine, m-anisidine, p-anisidine, N-methylaniline, N,N-dimethylaniline, N-ethylaniline, N,N-diethylaniline, and mixtures thereof.

Mixtures of any of the aforementioned amines may also be used in this disclosure.

In some embodiments of this invention, the at least one amine is selected from the group consisting of amine of the formula R$_3$N, heterocyclic amines, hydrazine and its derivatives, and mixtures thereof, wherein each R is independently a hydrogen, an alkyl group, a heteroalkyl group, an aryl group, or an aralkyl group.

In some embodiments of this invention, the at least one amine is selected from the group consisting of amine of the formula R$_3$N, heterocyclic amines, and mixtures thereof, wherein each R is independently a hydrogen, an alkyl group, a heteroalkyl group, or an aralkyl group.

In the processes of removing the R$_f$C≡CX impurity from the fluoroolefin, sterically hindered amines, such as triphenylamine, 2,2,6,6-tetramethylpiperidine (TMP), and 2,2,6,6-tetramethyl-4-piperidinol might not be as effective as other amines. In some embodiments of this invention, the at least one amine does not include the sterically hindered amines. In some embodiments of this invention, the at least one amine does not include triphenylamine, 2,2,6,6-tetramethylpiperidine, and 2,2,6,6-tetramethyl-4-piperidinol.

In some embodiments of this invention, the at least one amine is in a solution with a suitable solvent during the contacting step. A suitable solvent in this disclosure means an inert solvent in which the at least one amine is at least partially soluble. The term "inert" herein means that the solvent shall not react with amine or fluoroolefin during the contacting step.

In some embodiments of this invention, the suitable solvent is selected from the group consisting of water, hydrocarbons, ethers, alcohols (including glycols), benzene and its derivatives, alkyl halides, alkyl nitriles, amides, sulfoxides, sulfones, phosphate esters, and mixtures thereof.

In some embodiments of this invention, the suitable solvent is selected from the group consisting of water, ethers, alcohols (including glycols), benzene and its derivatives, alkyl halides, alkyl nitriles, amides, sulfoxides, sulfones, and mixtures thereof Examples of ether include acyclic alkyl ethers, cyclic ethers, perfluorinated ethers, glyme, diglyme, triglyme, tetraglyme, and mixtures thereof. Examples of acyclic alkyl ether include dimethyl ether, diethyl ether, methyl ethyl ether, and mixtures thereof. Examples of cyclic ether include 2-methyltetrahydrofuran, tetrahydrofuran, tetrahydropyran, 1,4-dioxane, and mixtures thereof. Examples of perfluorinated ether include perfluoro-N-methyl morpholine, perfluorotetrahydrofuran, and mixtures thereof.

Examples of alcohol include alkyl alcohols, glycols, glycerol, and mixtures thereof. Examples of alkyl alcohol include methanol, ethanol, proponal, isopropanol, 2-methyl-2-propanol (tert-butanol), cyclohexanol, and mixtures thereof. Examples of glycol include ethylene glycol, propylene glycol, diethylene glycol, and mixtures thereof.

Examples of benzene and its derivatives include benzene, alkylbenzenes, halobenzenes, benzonitrile, phenol, anisole, biphenyl, nitrobenzene, and mixtures thereof. Examples of alkylbenzene include toluene, ethylbenzene, o-xylene, m-xylene, p-xylene, mesitylene, durene, 2-phenylhexane, and mixtures thereof. Examples of halobenzene include fluorobenzene, chlorobenzene, 1,2-dichlorobenzene, 1,4-dichlorobenzene, and mixtures thereof.

Examples of alkyl halide include dichloromethane, chloroform, carbon tetrachloride, chloroethane, 1,2-dichloroethane, and mixtures thereof.

Examples of alkyl nitrile include acetonitrile, propionitrile, butyronitrile, methyl glutaronitrile, adiponitrile, and mixtures thereof.

Examples of amide include N,N-dimethyl formamide, N,N-dimethyl acetamide, N-methyl-2-pyrrolidone, and mixtures thereof.

Examples of sulfoxide include dimethyl sulfoxide.

Examples of sulfone include sulfolane.

The contacting step of this disclosure can be carried out using well-known chemical engineering practices for scrubbing organic compounds, which includes continuous, semi-continuous or batch operations. In some embodiments of this invention, fluoroolefin containing R$_f$C≡CX impurity is mixed with amine, optionally in the presence of a suitable solvent, in a vessel equipped with an agitator. For example, fluoroolefin containing R$_f$C≡CX impurity may be contacted with amine, optionally in the presence of a suitable solvent, under a suitable amount of pressure to maintain liquid phase of the fluoroolefin and the amine in a vessel. The contents of the contacting vessel may be agitated to provide contact between the fluoroolefin and the amine. The fluoroolefin is then recovered by phase separation or distillation.

In some embodiments of this invention, the contacting step can be carried out by contacting a gaseous mixture of fluoroolefin and R$_f$C≡CX impurity with liquid amine (optionally in a solution with a suitable solvent). For example, the mixture comprising fluoroolefin and R$_f$C≡CX impurity may be bubbled into liquid amine (optionally in a solution with a suitable solvent) as a gas in a stirred vessel. The fluoroolefin is then allowed to leave the contacting vessel, optionally through a condenser, where it is collected for subsequent purification.

In some embodiments of this invention, the contacting step is conducted in a column packed with materials such as helices, rings, saddles, spheres or other formed shapes fabricated from glass, plastic, or ceramics. The mixture comprising fluoroolefin and R$_f$C≡CX impurity enters the bottom of the column as a vapor. The liquid amine (optionally in a solution with a suitable solvent) enters the top of the column, for example, by means of a pump connected to a reservoir of said liquid amine (optionally in a solution with a suitable solvent).

The $R_fC\equiv CX$ impurity in the fluoroolefin is then scrubbed off with the amine in the column and the fluoroolefin vapor, with reduced $R_fC\equiv CX$ impurity, passes out the top of the column and is then collected. The amine passes out the bottom of the column and returns to the reservoir.

Optionally, a phase transfer catalyst can be employed in the contacting step process to increase the efficiency of removing the $R_fC\equiv CX$ impurity from the fluoroolefin.

In some embodiments of this invention, the temperature during the contacting step is from about 0° C. to about 60° C. In some embodiments of this invention, the temperature during the contacting step is from about 10° C. to about 30° C. Typically, less reactive amines require relatively higher temperatures. The pressure during the contacting step is not critical and can be subatmospheric, atmospheric or superatmospheric. In some embodiments of this invention, the contacting step is carried out under superatmospheric pressure. In some embodiments of this invention, the contacting step is carried out under atmospheric pressure. The time of contact between the mixture comprising fluoroolefin and $R_fC\equiv CX$ impurity and the amine is not critical and typically may be on the order of about 0.1 seconds to about an hour. In some embodiments of this invention, the contact time is from about 0.1 seconds to about 10 minutes.

During the contacting step, the mixture of fluoroolefin and $R_fC\equiv CX$ impurity is scrubbed with amine in the contacting vessel, and the $R_fC\equiv CX$ impurity is removed. In some embodiments of this invention, the concentration of the at least one $R_fC\equiv CX$ impurity in the mixture is reduced to 200 ppm or less. In some embodiments of this invention, the concentration of the at least one $R_fC\equiv CX$ impurity in the mixture is reduced to 100 ppm or less. In some embodiments of this invention, the concentration of the at least one $R_fC\equiv CX$ impurity in the mixture is reduced to 50 ppm or less. In some embodiments of this invention, the concentration of the at least one $R_fC\equiv CX$ impurity in the mixture is reduced to 10 ppm or less. In some embodiments of this invention, the concentration of the at least one $R_fC\equiv CX$ impurity in the mixture is reduced to 2 ppm or less.

The fluoroolefin having reduced concentration of the $R_fC\equiv CX$ impurity obtained from the contacting step can be recovered using techniques well-known in the art, such as condensation, distillation or phase separation. In some embodiments of this invention, the fluoroolefin obtained from the contacting step may be contaminated with amine and can be purified by scrubbing with water or weak acidic solution. The resulting fluoroolefin may be dried with a molecular sieve and further purified by distillation. In some embodiments of this invention, the fluoroolefin obtained from the contacting step is recovered by fractional distillation to separate from amine and/or other contaminants. The amine distillate may be recycled for use in the contacting step.

In some embodiments of this invention, the recovered fluoroolefin is substantially free of the $R_fC\equiv CX$ impurity. In some embodiments of this invention, the recovered HFO-1234yf is substantially free of the $R_fC\equiv CX$ impurity. In some embodiments of this invention, the recovered HFO-1234ze is substantially free of the $R_fC\equiv CX$ impurity. In some embodiments of this invention, the recovered HFO-1243zf is substantially free of the $R_fC\equiv CX$ impurity. In some embodiments of this invention, the recovered HCFO-1233xf is substantially free of the $R_fC\equiv CX$ impurity. In some embodiments of this invention, the recovered HCFO-1233zd is substantially free of the $R_fC\equiv CX$ impurity.

The present disclosure also provides a process for making at least one hydrotetrafluoropropene product selected from the group consisting of $CF_3CF\equiv CH_2$, $CF_3CH\equiv CHF$, and mixtures thereof. The process comprises: (a) dehydrohalogenating at least one starting material selected from the group consisting of $CF_3CFClCH_3$, $CF_3CHFCH_2Cl$, $CF_3CHClCH_2F$, $CF_3CH_2CHFCl$, $CF_3CHFCH_2F$, $CF_3CH_2CF_2H$, $CF_3CF_2CH_3$, and mixtures thereof to produce a product mixture comprising $CF_3C\equiv CH$ impurity and said at least one hydrotetrafluoropropene product; (b) contacting said product mixture with at least one amine to reduce the concentration of said $CF_3C\equiv CH$ impurity in said product mixture; and (c) recovering said at least one hydrotetrafluoropropene product having reduced concentration of said $CF_3C\equiv CH$ impurity.

The present disclosure also provides a process for making at least one hydrochlorotrifluoropropene product selected from the group consisting of $CF_3CCl\equiv CH_2$, $CF_3CH\equiv CHCl$, and mixtures thereof. The process comprises: (a) dehydrohalogenating at least one starting material selected from the group consisting of $CF_3CCl_2CH_3$, $CF_3CHClCH_2Cl$, $CF_3CHClCH_2F$, $CF_3CH_2CHCl_2$, $CF_3CHFCH_2Cl$, $CF_3CFClCH_3$, $CF_3CH_2CHFCl$, and mixtures thereof to produce a product mixture comprising $CF_3C\equiv CH$ impurity and said at least one hydrochlorotrifluoropropene product; (b) contacting said product mixture with at least one amine to reduce the concentration of said $CF_3C\equiv CH$ impurity in said product mixture; and (c) recovering said at least one hydrochlorotrifluoropropene product having reduced concentration of said $CF_3C\equiv CH$ impurity.

In some embodiments of this invention, the dehydrohalogenation process is carried out by pyrolyzing (thermally dehydrohalogenating) the starting material to produce the hydrotetrafluoropropene or hydrochlorotrifluoropropene product. The term "pyrolyzing" or "pyrolysis", as used herein, means chemical change produced by heating in the absence of catalyst. By absence of catalyst is meant that no material or treatment is added to the pyrolysis reactor that increases the reaction rate by reducing the activation energy of the pyrolysis process.

Suitable reactors for pyrolysis may be of any shape consistent with the process. In some embodiments of this invention, the reactor is a cylindrical tube, either straight or coiled. Heat is applied to the outside of the tube, with the chemical reaction taking place on the inside of the tube. Of note are pyrolysis reactors wherein the flow of gases through the reactor is partially obstructed to cause back-mixing, i.e. turbulence, and thereby promote mixing of gases and good heat transfer. This partial obstruction can be conveniently obtained by placing packing within the interior of the reactor, filling its cross-section or by using perforated baffles. The reactor packing can be particulate or fibrillar, has an open structure like that of Raschig Rings or other packings with a high free volume to avoid the accumulation of coke and to minimize pressure drop, and permits a generally free flow of gas. In some embodiments of this invention, the reactor packing is in cartridge disposition for ease of insertion and removal. In some embodiments of this invention, the pyrolysis reactor is substantially empty which means that the free volume of the reaction zone is at least about 80%, preferably at least about 90%, and more preferably at least about 95%. The free volume is the volume of the reaction zone minus the volume of the material that makes up the reactor packing. In some embodiments of this invention, the pyrolysis reactor is comprised of materials which are resistant to corrosion including stainless steel, Hastelloy™, Inconel™, Monel™, gold, or gold-lined or quartz.

The dehydrohalogenation process of this disclosure can be either a dehydrofluorination process or a dehydrochlorination process depending on the starting material and the corresponding fluoroolefin product. Typically, the pyrolysis temperature for dehydrofluorination is higher than the one for dehydrochlorination. In some embodiments of this invention, the dehydrofluorinating pyrolysis is conducted at a temperature of from about 600° C. to about 900° C. In some embodiments of this invention, the dehydrochlorinating pyrolysis is conducted at a temperature of from about 400° C. to about 700° C. Pyrolysis processes have also been disclosed in U.S. Pat. No. 7,833,434, U.S. Patent Publication No. 2010-0105967, and U.S. Patent Publication No. 2010-0105967.

In some embodiments of this invention, the dehydrohalogenation process is carried out in the presence of a catalyst. Suitable catalysts for dehydrohalogenation include alumina, fluorided alumina, aluminum fluoride, aluminum chlorofluoride; metal compounds supported on alumina, fluorided alumina, aluminum fluoride, or aluminum chlorofluoride; chromium oxide ($Cr_2O_3$), fluorided chromium oxide, and cubic chromium trifluoride; oxides, fluorides, and oxyfluorides of magnesium, zinc and mixtures of magnesium and zinc and/or aluminum; lanthanum oxide and fluorided lanthanum oxide; carbon, and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof. In some embodiments of this invention, the dehydrohalogenation catalyst is selected from the group consisting of carbon, alumina, fluorided alumina, and mixtures thereof. In some embodiments of this invention, carbon includes acid-washed carbon, activated carbon and three dimensional matrix carbonaceous materials. In some embodiments of this invention, the dehydrohalogenation catalyst comprises alkali metal salt supported on chromium oxide. The catalytic dehydrohalogenation processes have also been disclosed in U.S. Pat. No. 7,943,015, U.S. Pat. No. 7,897,823, and U.S. Pat. No. 7,985,884.

In some embodiments of this invention, the dehydrohalogenation process is carried out by reacting the starting material with a basic aqueous solution to produce the hydrotetrafluoropropene or hydrochlorotrifluoropropene product. As used herein, the basic aqueous solution is a liquid that is primarily an aqueous liquid having a pH of over 7, and the liquid may be a solution, dispersion, emulsion, suspension or the like. In some embodiments of this invention, the basic aqueous solution has a pH of 8 or higher. In some embodiments of this invention, the basic aqueous solution has a pH of 10 or higher. Typically, a dehydrofluorination process needs a higher pH solution than a dehydrochlorination process.

In some embodiments of this invention, an inorganic base is used to form the basic aqueous solution. Such inorganic base can be selected from the group consisting of hydroxide, oxide, carbonate, and phosphate salts of alkali, alkaline earth metals and mixtures thereof. In some embodiments, such inorganic base is sodium hydroxide, potassium hydroxide, or mixtures thereof. In some embodiments of this invention, the basic aqueous solution is an aqueous solution of a quaternary ammonium hydroxide of the formula $NR'_4OH$ wherein each R' is independently hydrogen, a $C_1$ to $C_{16}$ alkyl group, aralkyl group, or substituted alkyl group, provided that not all R' are hydrogens. Examples of $NR'_4OH$ compound include tetra-n-butylammonium hydroxide, tetra-n-propylammonium hydroxide, tetraethylammonium hydroxide, tetramethylammonium hydroxide, benzyltrimethylammonium hydroxide, hexadecyltrimethyammonium hydroxide, choline hydroxide, and mixtures thereof.

Optionally, the starting material is reacted with the basic aqueous solution in the presence of an organic solvent. In some embodiments of this invention, the organic solvent is selected from the group consisting of benzene and its derivatives, alcohols, alkyl halides, alkyl nitriles, ethers, amides, ketones, sulfoxides, phosphate esters and mixtures thereof.

Optionally, the starting material is reacted with the basic aqueous solution in the presence of a phase transfer catalyst. The phase transfer catalyst used herein can facilitate the transfer of ionic compounds into an organic phase from an aqueous phase and facilitate the reaction between water-soluble and water-insoluble reaction components.

The dehydrohalogenation using a basic aqueous solution has also been disclosed in PCT Publication No. WO2010/129844.

In some embodiments of this invention, during the dehydrohalogenating step, starting materials selected from the group consisting of $CF_3CFClCH_3$ (HCFC-244bb), $CF_3CHFCH_2Cl$ (HCFC-244eb), $CF_3CHClCH_2F$ (HCFC-244db), $CF_3CH_2CHFCl$ (HCFC-244fa), $CF_3CHFCH_2F$ (HFC-245eb), $CF_3CH_2CF_2H$ (HFC-245fa), and $CF_3CF_2CH_3$ (HFC-245cb) are dehydrohalogenated to form either $CF_3CF=CH_2$ or $CF_3CH=CHF$ product. In some embodiments of this invention, the at least one starting material is selected from the group consisting of $CF_3CFClCH_3$, $CF_3CHFCH_2Cl$, $CF_3CHFCH_2F$, $CF_3CF_2CH_3$, and mixtures thereof, and the at least one hydrotetrafluoropropene product is $CF_3CF=CH_2$. In some embodiments of this invention, the at least one starting material is $CF_3CFClCH_3$, and the at least one hydrotetrafluoropropene product is $CF_3CF=CH_2$ (i.e., the starting material $CF_3CFClCH_3$ is dehydrochlorinated to produce a product mixture comprising $CF_3CF=CH_2$ product and $CF_3C\equiv CH$ impurity). In some embodiments of this invention, the at least one starting material is $CF_3CHFCH_2F$, and the at least one hydrotetrafluoropropene product is $CF_3CF=CH_2$ (i.e., the starting material $CF_3CHFCH_2F$ is dehydrofluorinated to produce a product mixture comprising $CF_3CF=CH_2$ product and $CF_3C\equiv CH$ impurity). In some embodiments of this invention, the at least one starting material is selected from the group consisting of $CF_3CH_2CHF_2$, $CF_3CH_2CHFCl$, $CF_3CHClCH_2F$, and mixtures thereof, and the at least one hydrotetrafluoropropene product is $CF_3CH=CHF$.

In some embodiments of this invention, during the dehydrohalogenating step, starting materials selected from the group consisting of $CF_3CCl_2CH_3$ (HCFC-243ab), $CF_3CHClCH_2Cl$ (HCFC-243db), $CF_3CHClCH_2F$ (HCFC-244db), $CF_3CH_2CHCl_2$ (HCFC-243fa), $CF_3CHFCH_2Cl$ (HCFC-244eb), $CF_3CFClCH_3$ (HCFC-244bb), and $CF_3CH_2CHFCl$ (HCFC-244fa) are dehydrohalogenated to form either $CF_3CCl=CH_2$ or $CF_3CH=CHCl$ product. In some embodiments of this invention, the at least one starting material is selected from the group consisting of $CF_3CHClCH_2Cl$, $CF_3CH_2CHCl_2$, and mixtures thereof, and the at least one hydrochlorotrifluoropropene product is $CF_3CH=CHCl$ (i.e., the at least one starting material selected from the group consisting of $CF_3CHClCH_2Cl$, $CF_3CH_2CHCl_2$, and mixtures thereof is dehydrochlorinated to produce a product mixture comprising $CF_3CH=CHCl$ product and $CF_3C\equiv CH$ impurity). In some embodiments of this invention, the at least one starting material is selected from the group consisting of $CF_3CHClCH_2Cl$, $CF_3CCl_2CH_3$, and mixtures thereof, and the at least one hydrochlorotrifluoropropene product is $CF_3CHCl=CH_2$ (i.e., the at least one starting material selected from the group consisting of $CF_3CHClCH_2Cl$, $CF_3CCl_2CH_3$, and mixtures thereof is dehydrochlorinated to produce a product mixture comprising $CF_3CHCl\!=\!CH_2$ product and $CF_3C\!\equiv\!CH$ impurity).

During the dehydrohalogenating step, byproduct $CF_3C\!\equiv\!CH$ is also generated. During the contacting step, the product mixture of hydrotetrafluoropropene or hydrochlorotrifluoropropene product and $CF_3C\!\equiv\!CH$ impurity is scrubbed with amine using the contacting step processes as described in this disclosure. In some embodiments of this invention, the at least one amine employed in the contacting step (b) to remove the $CF_3C\!\equiv\!CH$ impurity from the hydrotetrafluoropropene or hydrochlorotrifluoropropene product mixture is selected from the group consisting of amine of the formula $R_3N$, heterocyclic amines, hydrazine and its derivatives, and mixtures thereof, wherein each R is independently a hydrogen, an alkyl group, a heteroalkyl group, an aryl group, or an aralkyl group. In some embodiments of this invention, the at least one amine employed in the contacting step (b) is selected from the group consisting of amine of the formula $R_3N$, heterocyclic amines, and mixtures thereof, wherein each R is independently a hydrogen, an alkyl group, a heteroalkyl group, or an aralkyl group.

In some embodiments of this invention, the concentration of the $CF_3C\!\equiv\!CH$ impurity in the hydrotetrafluoropropene or hydrochlorotrifluoropropene product mixture is reduced to 200 ppm or less in the contacting step (b). In some embodiments of this invention, the concentration of the $CF_3C\!\equiv\!CH$ impurity in the hydrotetrafluoropropene or hydrochlorotrifluoropropene product mixture is reduced to 100 ppm or less in the contacting step (b). In some embodiments of this invention, the concentration of the $CF_3C\!\equiv\!CH$ impurity in the hydrotetrafluoropropene or hydrochlorotrifluoropropene product mixture is reduced to 50 ppm or less in the contacting step (b). In some embodiments of this invention, the concentration of the $CF_3C\!\equiv\!CH$ impurity in the hydrotetrafluoropropene or hydrochlorotrifluoropropene product mixture is reduced to 10 ppm or less in the contacting step (b). In some embodiments of this invention, the concentration of the $CF_3C\!\equiv\!CH$ impurity in the hydrotetrafluoropropene or hydrochlorotrifluoropropene product mixture is reduced to 2 ppm or less in the contacting step (b).

In some embodiments of this invention, the concentration of the $CF_3C\!\equiv\!CH$ impurity in the product mixture comprising $CF_3C\!\equiv\!CH$ impurity and $CF_3CF\!=\!CH_2$ product is reduced to 200 ppm or less in the contacting step (b). In some embodiments of this invention, the concentration of the $CF_3C\!\equiv\!CH$ impurity in the product mixture comprising $CF_3C\!\equiv\!CH$ impurity and $CF_3CF\!=\!CH_2$ product is reduced to 100 ppm or less in the contacting step (b). In some embodiments of this invention, the concentration of the $CF_3C\!\equiv\!CH$ impurity in the product mixture comprising $CF_3C\!\equiv\!CH$ impurity and $CF_3CF\!=\!CH_2$ product is reduced to 50 ppm or less in the contacting step (b). In some embodiments of this invention, the concentration of the $CF_3C\!\equiv\!CH$ impurity in the product mixture comprising $CF_3C\!\equiv\!CH$ impurity and $CF_3CF\!=\!CH_2$ product is reduced to 10 ppm or less in the contacting step (b). In some embodiments of this invention, the concentration of the $CF_3C\!\equiv\!CH$ impurity in the product mixture comprising $CF_3C\!\equiv\!CH$ impurity and $CF_3CF\!=\!CH_2$ product is reduced to 2 ppm or less in the contacting step (b).

In some embodiments of this invention, the concentration of the $CF_3C\!\equiv\!CH$ impurity in the product mixture comprising $CF_3C\!\equiv\!CH$ impurity and $CF_3CH\!=\!CHF$ product is reduced to 200 ppm or less in the contacting step (b). In some embodiments of this invention, the concentration of the $CF_3C\!\equiv\!CH$ impurity in the product mixture comprising $CF_3C\!\equiv\!CH$ impurity and $CF_3CH\!=\!CHF$ product is reduced to 100 ppm or less in the contacting step (b). In some embodiments of this invention, the concentration of the $CF_3C\!\equiv\!CH$ impurity in the product mixture comprising $CF_3C\!\equiv\!CH$ impurity and $CF_3CH\!=\!CHF$ product is reduced to 50 ppm or less in the contacting step (b). In some embodiments of this invention, the concentration of the $CF_3C\!\equiv\!CH$ impurity in the product mixture comprising $CF_3C\!\equiv\!CH$ impurity and $CF_3CH\!=\!CHF$ product is reduced to 10 ppm or less in the contacting step (b). In some embodiments of this invention, the concentration of the $CF_3C\!\equiv\!CH$ impurity in the product mixture comprising $CF_3C\!\equiv\!CH$ impurity and $CF_3CH\!=\!CHF$ product is reduced to 2 ppm or less in the contacting step (b).

The hydrotetrafluoropropene or hydrochlorotrifluoropropene product obtained from the contacting step (b) can be recovered using the recovering step processes as described in this disclosure. In some embodiments of this invention, various azeotropic or azeotrope-like (i.e., near azeotrope) compositions of the hydrotetrafluoropropene or hydrochlorotrifluoropropene product may be utilized in the processes of recovering these products. For example, HF can be added to the HFO-1234yf product mixture obtained from the contacting step (b), and separation of HFO-1234yf includes isolation of azeotrope or near azeotrope of HFO-1234yf and HF and further processing to produce HF-free HFO-1234yf by using procedures similar to that disclosed in U.S. Pat. No. 7,897,823. Azeotrope or near azeotrope compositions of HFO-1234yf and HF have been disclosed in U.S. Pat. No. 7,476,771. For another example, HF can be added to the HFO-1234ze product mixture obtained from the contacting step (b), and separation of HFO-1234ze includes isolation of azeotrope or near azeotrope of HFO-1234ze and HF and further processing to produce HF-free HFO-1234ze by using procedures similar to that disclosed in U.S. Pat. No. 7,897,823. U.S. Pat. No. 7,423,188 discloses azeotrope or near-azeotrope compositions of the E-isomer of HFO-1234ze and HF, and U.S. Patent Publication No. 2010-0200798 discloses azeotrope or near-azeotrope compositions of the Z-isomer of HFO-1234ze and HF. For another example, HF can be added to the HCFO-1233xf product mixture obtained from the contacting step (b), and separation of HCFO-1233xf includes isolation of azeotrope or near azeotrope of HCFO-1233xf and HF and further processing to produce HF-free HCFO-1233xf by using procedures similar to that disclosed in U.S. Pat. No. 7,897,823. The azeotrope compositions of HCFO-1233xf and HF has been disclosed in U.S. Patent Publication No. 2010-0072415. For another example, HF can be added to the HCFO-1233zd product mixture obtained from the contacting step (b), and separation of HCFO-1233zd includes isolation of azeotrope or near azeotrope of HCFO-1233zd and HF and further processing to produce HF-free HCFO-1233zd by using procedures similar to that disclosed in U.S. Pat. No. 7,897,823. Some azeotrope compositions of HCFO-1233zd and HF have been disclosed in U.S. Pat. No. 6,013,846.

In some embodiments of this invention, the recovered hydrotetrafluoropropene or hydrochlorotrifluoropropene product is substantially free of the $CF_3C\!\equiv\!CH$ impurity. In some embodiments of this invention, the recovered HFO-1234yf product is substantially free of the $CF_3C\!\equiv\!CH$ impurity. In some embodiments of this invention, the recovered HFO-1234ze product is substantially free of the $CF_3C\!\equiv\!CH$ impurity.

The contacting vessels, reactors, distillation columns, and their associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Many aspects and embodiments have been described above and are merely exemplary and not limiting. After reading this specification, skilled artisans appreciate that other aspects and embodiments are possible without departing from the scope of the invention.

Examples

The concepts described herein will be further described in the following examples, which do not limit the scope of the invention described in the claims.

The term "% by GC-MS", as used herein, means the percentage of the peak area measured on the GC-MS spectrum.

The term "% by GC-FID", as used herein, means the percentage of the peak area measured on the GC-FID spectrum.

Example 1

Example 1 demonstrates that HFO-1234yf can become substantially free of the $CF_3C\equiv CH$ impurity after contacting with ethylene diamine.

A gaseous HFO-1234yf sample, which was analyzed by GC and GC-MS to contain 0.222% by GC-FID of the $CF_3C\equiv CH$ impurity, was bubbled through a scrubber containing about 100 ml ethylene diamine at a flow rate of 16 sccm at room temperature. The effluent gas from the scrubber was analyzed by GC and GC-MS again to show that the concentration of the $CF_3C\equiv CH$ impurity contained in the HFO-1234yf sample dropped to non-detectable level. The analysis results are also listed in Table 1.

Example 2

Example 2 demonstrates that HFO-1234yf can become substantially free of the $CF_3C\equiv CH$ impurity after contacting with morpholine.

A gaseous HFO-1234yf sample, which was analyzed by GC and GC-MS to contain 0.181% by GC-FID of the $CF_3C\equiv CH$ impurity, was bubbled through a scrubber containing about 100 ml morpholine at a flow rate of 20 sccm at room temperature. The effluent gas from the scrubber was analyzed by GC and GC-MS again to show that the concentration of the $CF_3C\equiv CH$ impurity contained in the HFO-1234yf sample dropped to non-detectable level. The analysis results are also listed in Table 1.

Example 3

Example 3 demonstrates that the concentration of the $CF_3C\equiv CH$ impurity contained in HFO-1234yf can be largely reduced by contacting with ethanolamine A gaseous HFO-1234yf sample, which was analyzed by GC and GC-MS to contain 0.202% by GC-FID of the $CF_3C\equiv CH$ impurity, was bubbled through a scrubber containing about 100 ml ethanolamine at a flow rate of 16 sccm at room temperature. The effluent gas from the scrubber was analyzed by GC and GC-MS again to show that the concentration of the $CF_3C\equiv CH$ impurity contained in the HFO-1234yf sample dropped to 0.049% by GC-FID. The analysis results are also listed in Table 1.

Example 4

Example 4 demonstrates that the concentration of the $CF_3C\equiv CH$ impurity contained in HFO-1234yf can be largely reduced by contacting with triethylamine.

A gaseous HFO-1234yf sample, which was analyzed by GC and GC-MS to contain 0.200% by GC-FID of the $CF_3C\equiv CH$ impurity, was bubbled through a scrubber containing about 100 ml triethylamine at a flow rate of 16 sccm at room temperature. The effluent gas from the scrubber was analyzed by GC and GC-MS again to show that the concentration of the $CF_3C\equiv CH$ impurity contained in the HFO-1234yf sample dropped to 0.095% by GC-FID. The analysis results are also listed in Table 1.

Example 5

Example 5 demonstrates that the concentration of the $CF_3C\equiv CH$ impurity contained in HFO-1234yf can be largely reduced by contacting with pyridine.

A gaseous HFO-1234yf sample, which was analyzed by GC and GC-MS to contain 0.187% by GC-FID of the $CF_3C\equiv CH$ impurity, was bubbled through a scrubber containing about 100 ml pyridine at a flow rate of 16 sccm at room temperature. The effluent gas from the scrubber was analyzed by GC and GC-MS again to show that the concentration of the $CF_3C\equiv CH$ impurity contained in the HFO-1234yf sample dropped to 0.081% by GC-FID. The analysis results are also listed in Table 1.

TABLE 1

| Example No. | Scrubber Amine | Length (inch) | $CF_3C\equiv CH$ Concentration (% by GC-FID) Before Scrubbing | After Scrubbing | Flow Rate (sccm) |
| --- | --- | --- | --- | --- | --- |
| 1 | ethylene diamine | 2.25 | 0.222 | ND | 16 |
| 2 | morpholine | 2.25 | 0.181 | ND | 20 |
| 3 | ethanolamine | 2.125 | 0.202 | 0.049 | 16 |
| 4 | triethylamine | 2.5 | 0.200 | 0.095 | 16 |
| 5 | pyridine | 2.25 | 0.187 | 0.081 | 16 |

ND = non-detectable, which means 2 ppm-molar or less.

Example 6

Example 6 demonstrates that HCFO-1224yd can become substantially free of the $CF_3C\equiv CCl$ impurity after contacting with pyridine.

A sealed 240 ml cylinder containing a 148.7 g HCFO-1224yd sample with 1.026% by GC-MS $CF_3C\equiv CCl$ impurity was cooled to about 0° C. and was charged with 0.5 ml pyridine via a syringe. The cylinder was then warmed up to room temperature and was shaken for 10 minutes. After another two hours, the HCFO-1224yd sample was analyzed by GC-MS to show that the concentration of the $CF_3C\equiv CCl$ impurity contained in the HCFO-1224yd sample had dropped to non-detectable level.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A process comprising: contacting a mixture comprising at least one fluoroolefin and at least one $R_fC$=$CX$ impurity with at least one amine to reduce the concentration of said at least one $R_fC$=$CX$ impurity in said mixture; wherein $R_f$ is a perfluorinated alkyl group, and X is H, F, Cl, Br or I.

2. The process of claim 1 wherein the amount of said at least one fluoroolefin in said mixture is at least 90 wt % based on the total weight of said mixture.

3. The process of claim 1 wherein said at least one fluoroolefin is selected from the group consisting of $CF_3CF$=$CH_2$, $CF_3CH$=$CHF$, $CF_3CH$=$CH_2$, $CF_3CCl$=$CH_2$, $CF_3CH$=$CHCl$, $CF_3CH$=$CFCl$, $CF_3CH$=$CF_2$, $CF_3CCl$=$CHF$, $CF_3CF$=$CHF$, $CF_3CF$=$CHCl$, $CF_3CH$=$CCl_2$, $CF_3CCl$=$CHCl$, and mixtures thereof, and wherein said at least one $R_fC$=$CX$ impurity is selected from the group consisting of $CF_3C$=$CH$, $CF_3C$=$CCl$, $CF_3C$=$CF$, and mixtures thereof.

4. The process of claim 1 wherein said at least one fluoroolefin is selected from the group consisting of $CF_3CF$=$CH_2$, $CF_3CH$=$CHF$, $CF_3CH$=$CH_2$, $CF_3CCl$=$CH_2$, $CF_3CH$=$CHCl$, $CF_3CF$=$CHCl$, and mixtures thereof, and wherein said at least one $R_fC$=$CX$ impurity is selected from the group consisting of $CF_3C$=$CH$, $CF_3C$=$CCl$, $CF_3C$=$CF$, and mixtures thereof.

5. The process of claim 1 wherein said at least one fluoroolefin is selected from the group consisting of $CF_3CF$=$CH_2$, $CF_3CH$=$CHF$, $CF_3CCl$=$CH_2$, $CF_3CH$=$CHCl$, and mixtures thereof, and wherein said at least one $R_fC$=$CX$ impurity is selected from the group consisting of $CF_3C$=$CH$, $CF_3C$=$CCl$, and mixtures thereof.

6. The process of claim 1 wherein said at least one fluoroolefin is $CF_3CF$=$CH_2$, and wherein said at least one $R_fC$=$CX$ impurity is selected from the group consisting of $CF_3C$=$CH$, $CF_3C$=$CCl$, and mixtures thereof.

7. The process of claim 1 wherein said at least one fluoroolefin is $CF_3CF$=$CH_2$, and wherein said at least one $R_fC$=$CX$ impurity is $CF_3C$=$CH$.

8. The process of claim 1 wherein said at least one fluoroolefin is $CF_3CH$=$CHF$, and wherein said at least one $R_fC$=$CX$ impurity is $CF_3C$=$CH$.

9. The process of claim 1 wherein said at least one fluoroolefin is a mixture of $CF_3CF$=$CH_2$ and $CF_3CH$=$CHF$, and wherein said at least one $R_fC$=$CX$ impurity is $CF_3C$=$CH$.

10. The process of claim 1 wherein said at least one fluoroolefin is $CF_3CH$=$CHCl$, and wherein said at least one $R_fC$=$CX$ impurity is $CF_3C$=$CH$.

11. The process of claim 1 wherein said at least one amine is selected from the group consisting of amine of the formula $R_3N$, heterocyclic amines, hydrazine and its derivatives, and mixtures thereof, wherein each R is independently a hydrogen, an alkyl group, a heteroalkyl group, an aryl group, or an aralkyl group.

12. The process of claim 1 wherein said at least one amine is selected from the group consisting of amine of the formula $R_3N$, heterocyclic amines, and mixtures thereof, wherein each R is independently a hydrogen, an alkyl group, a heteroalkyl group, or an aralkyl group.

13. The process of claim 12 wherein said at least one amine is a polyamine.

14. The process of claim 12 wherein said at least one amine is a heterocyclic amine.

15. The process of claim 1 wherein said at least one amine is in a solution with a suitable solvent during said contacting step.

16. The process of claim 1 wherein the temperature during said contacting step is from about 0° C. to about 60° C.

17. The process of claim 1 wherein the concentration of said at least one $R_fC$=$CX$ impurity in said mixture is reduced to 200 ppm or less.

18. The process of claim 1 wherein the concentration of said at least one $R_fC$=$CX$ impurity in said mixture is reduced to 50 ppm or less.

19. The process of claim 1 wherein the concentration of said at least one $R_fC$=$CX$ impurity in said mixture is reduced to 2 ppm or less.

20. The process of claim 1 further comprising recovering said at least one fluoroolefin having reduced concentration of said at least one $R_fC$=$CX$ impurity.

21. A process for making at least one hydrotetrafluoropropene product selected from the group consisting of $CF_3CF$=$CH_2$, $CF_3CH$=$CHF$, and mixtures thereof, comprising:
 (a) dehydrohalogenating at least one starting material selected from the group consisting of $CF_3CFClCH_3$, $CF_3CHFCH_2Cl$, $CF_3CHClCH_2F$, $CF_3CH_2CHFCl$, $CF_3CHFCH_2F$, $CF_3CH_2CF_2H$, $CF_3CF_2CH_3$, and mixtures thereof to produce a product mixture comprising $CF_3C$=$CH$ impurity and said at least one hydrotetrafluoropropene product;
 (b) contacting said product mixture with at least one amine to reduce the concentration of said $CF_3C$=$CH$ impurity in said product mixture; and
 (c) recovering said at least one hydrotetrafluoropropene product having reduced concentration of said $CF_3C$=$CH$ impurity.

22. The process of claim 21 wherein said at least one hydrotetrafluoropropene product is $CF_3CF$=$CH_2$, and said at least one starting material is selected from the group consisting of $CF_3CFClCH_3$, $CF_3CHFCH_2Cl$, $CF_3CHFCH_2F$, $CF_3CF_2CH_3$, and mixtures thereof.

23. The process of claim 22 wherein said at least one starting material is $CF_3CFClCH_3$.

24. The process of claim 22 wherein said at least one starting material is $CF_3CHFCH_2F$.

25. The process of claim 21 wherein said at least one hydrotetrafluoropropene product is $CF_3CH$=$CHF$, and said at least one starting material is selected from the group consisting of $CF_3CH_2CHF_2$, $CF_3CH_2CHFCl$, $CF_3CHClCH_2F$, and mixtures thereof.

26. The process of claim 21, wherein the concentration of said $CF_3C$=$CH$ impurity in said product mixture is reduced to 200 ppm or less in the contacting step (b).

27. A process for making at least one hydrochlorotrifluoropropene product selected from the group consisting of $CF_3CCl$=$CH_2$, $CF_3CH$=$CHCl$, and mixtures thereof, comprising:

(a) dehydrohalogenating at least one starting material selected from the group consisting of $CF_3CCl_2CH_3$, $CF_3CHClCH_2Cl$, $CF_3CHClCH_2F$, $CF_3CH_2CHCl_2$, $CF_3CHFCH_2Cl$, $CF_3CFClCH_3$, $CF_3CH_2CHFCl$, and mixtures thereof to produce a product mixture comprising $CF_3C{\equiv}CH$ impurity and said at least one hydrochlorotrifluoropropene product;

(b) contacting said product mixture with at least one amine to reduce the concentration of said $CF_3C{\equiv}CH$ impurity in said product mixture; and (c) recovering said at least one hydrochlorotrifluoropropene product having reduced concentration of said $CF_3C{\equiv}CH$ impurity.

28. The process of claim 27 wherein at least one hydrochlorotrifluoropropene product is $CF_3CH{=}CHCl$, and said at least one starting material is selected from the group consisting of $CF_3CHClCH_2Cl$, $CF_3CH_2CHCl_2$, and mixtures thereof.

29. The process of claim 27 wherein at least one hydrochlorotrifluoropropene product is $CF_3CHCl{=}CH_2$, and said at least one starting material is selected from the group consisting of $CF_3CHClCH_2Cl$, $CF_3CCl_2CH_3$, and mixtures thereof.

30. The process of claim 27, wherein the concentration of said $CF_3C{\equiv}CH$ impurity in said product mixture is reduced to 200 ppm or less in the contacting step (b).

31. The process of claim 21, wherein said at least one amine is selected from the group consisting of amine of the formula $R_3N$, heterocyclic amines, and mixtures thereof, wherein each R is independently a hydrogen, an alkyl group, a heteroalkyl group, or an aralkyl group.

* * * * *